(12) United States Patent
Palmer (10) Patent No.: US 6,561,192 B2
(45) Date of Patent: May 13, 2003

(54) NASAL ORAL RESPIRATORY INTERFACE

(75) Inventor: Charles Palmer, Hummelstown, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/798,021

(22) Filed: Mar. 1, 2001

(65) Prior Publication Data

US 2001/0029954 A1 Oct. 18, 2001

Related U.S. Application Data

(60) Provisional application No. 60/186,859, filed on Mar. 3, 2000, and provisional application No. 60/201,935, filed on May 5, 2000.

(51) Int. Cl.$^7$ .............................................. A61M 16/00
(52) U.S. Cl. .............................. 128/207.17; 128/207.14
(58) Field of Search ....................... 128/207.14, 207.15, 128/207.17, 207.18, 200.24, 200.26, 911, 912, DIG. 26; 604/174, 180

(56) References Cited

U.S. PATENT DOCUMENTS

| 3,993,081 A | 11/1976 | Cussell | |
|---|---|---|---|
| 4,142,527 A | 3/1979 | Garcia | |
| 4,223,671 A | * | 9/1980 | Muto ..................... 128/200.26 |

(List continued on next page.)

FOREIGN PATENT DOCUMENTS

WO   PCT/US01/066404   9/2001

OTHER PUBLICATIONS

Extubation and Reintubation in the NICU: Identifying Opportunities to Improve Care (Linda Sturla Franck, Barbara Vaughan, Jeanette Wallace).

The "Handy Bar": Endotracheal Tube Stabilizing Bar (Tony R. Van Deventer, MS, RRT).

A Comparision of Two Methods of Oral Endotracheal Tube Stabilization in Neonatal Patients (Mitchell H. DeJonge, MD, Melissa White, RNC, MS).

Primary Examiner—Aaron J. Lewis
Assistant Examiner—Teena Mitchell
(74) Attorney, Agent, or Firm—McKee, Voorhees & Sease, P.L.C.

(57) ABSTRACT

The present invention provides an apparatus and a method for stabilizing at least one medical device such as a tracheal or gastric tube entering or covering at least one facial cavity such as the mouth and/or nose, taking advantage of a stabilization stent to secure to a patient's face the tracheal or gastric tube without the need to apply tape to the face, while maintaining visibility of tube markings, preventing kinking of the tube, and keeping the infant's face visible to parents and caregivers. In one form, the invention comprises a transverse stent comprising a superior border opposed to an inferior border, an inner surface and an outer surface. A first facial interface is attached to a first terminal end of the transverse stent, and positioned to adhesively adhere and mechanically clasp to a first side of a patient's face. A second facial interface is attached to a second terminal end of the transverse stent and positioned to adhesively adhere and mechanically clasp to a second side of a patient's face. A docking platform attached to the outer surface of the transverse stent supports the medical device. In a different form, the invention also includes gutters positioned on the inner surface of the respective first and second terminal end approximate to the respective first and second facial interface to channel oral fluids away from the respective first and second facial interface. The outer surface contains channels for containing and directing tubing, and fixaton points for attaching anchoring measures such as chin or head straps. The core of the transverse stent is hollowed to permit gas flow.

64 Claims, 5 Drawing Sheets

U.S. PATENT DOCUMENTS

| | | | |
|---|---|---|---|
| 4,284,076 A | | 8/1981 | Hall |
| 4,516,293 A | * | 5/1985 | Beran .................... 128/207.17 |
| 4,537,192 A | * | 8/1985 | Foster ................... 128/207.14 |
| 4,683,882 A | | 8/1987 | Laird |
| 4,742,824 A | | 5/1988 | Payton et al. |
| 4,744,358 A | * | 5/1988 | McGinnis .............. 128/207.17 |
| 5,009,227 A | * | 4/1991 | Nieuwstad ............. 128/207.17 |
| 5,117,818 A | | 6/1992 | Palfy |
| 5,232,453 A | | 8/1993 | Plass et al. |
| 5,263,941 A | | 11/1993 | Cockrill |
| 5,269,296 A | | 12/1993 | Landis |
| 5,345,931 A | | 9/1994 | Battaglia, Jr. |
| 5,419,319 A | | 5/1995 | Werner |
| 5,437,273 A | | 8/1995 | Bates et al. |
| 5,458,139 A | | 10/1995 | Pearl |
| 5,490,504 A | | 2/1996 | Vrona et al. |
| 5,513,633 A | * | 5/1996 | Islava .................... 128/207.17 |
| 5,513,634 A | * | 5/1996 | Jackson ................. 128/207.18 |
| 5,533,504 A | * | 7/1996 | Stamos .................. 128/201.18 |
| 5,533,506 A | | 7/1996 | Wood |
| 5,546,938 A | | 8/1996 | McKenzie |
| 5,558,090 A | | 9/1996 | James |
| 5,626,565 A | | 5/1997 | Landis et al. |
| 5,682,881 A | * | 11/1997 | Winthrop et al. ...... 128/207.18 |
| 5,782,236 A | | 7/1998 | Ess |
| 5,797,394 A | | 8/1998 | Boyd |
| 5,803,079 A | * | 9/1998 | Rogers et al. ......... 128/207.14 |
| 5,810,000 A | | 9/1998 | Stevens |
| 5,934,276 A | * | 8/1999 | Fabro et al. ........... 128/207.17 |
| 6,010,484 A | * | 1/2000 | McCormick et al. ....... 604/174 |
| 6,026,811 A | | 2/2000 | Settle |
| 6,029,668 A | | 2/2000 | Freed |
| 6,050,263 A | | 4/2000 | Choksi et al. |
| 6,067,985 A | | 5/2000 | Islava |
| 6,105,573 A | | 8/2000 | Delaplane et al. |
| 6,105,577 A | | 8/2000 | Varner |

* cited by examiner

NASAL ORAL RESPIRATORY INTERFACE

CROSS REFERENCE TO RELATED APPLICATIONS

This application claims benefit of U.S. Provisional Application Nos. 60/186,859 filed Mar. 3, 2000 and 60/201,935 filed May 5, 2000.

FIELD OF THE INVENTION

This invention relates generally to stabilization of medical devices, and more particularly to stabilization of devices that enter or cover the nose and/or mouth. Although most useful in a neonatal intensive care unit (NICU) setting, the advantages of the present invention are applicable to any patient age group or setting requiring such stabilization.

BACKGROUND OF THE INVENTION

Infants requiring mechanical ventilation (assisted breathing) are commonly treated by endotracheal intubation, wherein a flexible tube is inserted into the mouth, down the throat and through the lumen of the trachea a predetermined distance, to deliver oxygen to the lungs. In addition, flexible feeding tubes may also be inserted through the nose or mouth, passing through the esophagus, and terminating in the stomach or lower intestinal tract.

Serious complications can result from accidental extubation (dislodgment) of these tubes, including acute hypoxia, bradycardia, and long term laryngaltracheal damage from reintubation. Therefore, it is critical to prevent accidental extubation. Traditionally, stabilization to prevent accidental extubation has been accomplished by securing the tube to the face by wrapping an adhesive tape around the tube and adhering the tape ends to the patient's face.

However, adhesive tape stabilization methods provide poor fixation, allowing the tube to move when the skin is stretched. The tape obstructs the face, has the potential to obstruct the nasal openings, and loosens with time. Tape is difficult to remove and reapply when adjustments to the tubes are required, often causing injuries to the skin by stripping away the epidermis, especially in premature infants. Tape adhesion methods have a further disadvantage, in that nasal and oral secretions are absorbed by the tape, causing the tape to lose adhesion and loosen, while contaminating the tape with microbial organisms that could colonize the patient and gain direct access to the lung via the endotracheal tube and cause pneumonia.

Mechanical ventilation applies a pulling force on the tubing. As a result of this pulling force, an improperly stabilized tube may cause pain and discomfort if the tube slides up and down within the trachea, especially if it hits against the bifurcation of the trachea. Moreover if the tube protruding outside the patient kinks, gas flow will be obstructed. Movement of the tube may cause it to extend and enter the right main bronchus, effectively removing the supply of oxygen to the left lung, or it may extubate completely, removing the supply of oxygen entirely. Such movement of the endotracheal tube in the small premature infant is a major clinical problem. In these patients the trachea is so short there may be only a few millimeters of discretionary tube movement before one of the above complications ensues.

Systems used to increase tube stabilization and limit tube movement have included bite block and neck strap combinations to fix the tube in position; a band extending across and adhered to the full width of the infant's face, wherein the band contains tube receiving receptacles at predetermined locations; adhesive straps with a central opening over the mouth containing various tube locking means; and a flexible bar placed above the mouth and adhered to the infant's cheeks.

With the exception of the bar, these known stabilization attempts have covered the patient's mouth and portions of the tube, making oral hygiene and tube visualization difficult. These devices further require the endotracheal tube be placed within the device prior to intubation, thereby blocking the clinician's visualization of the trachea and increasing the difficulty of successfully placing the tube in its desired location, making the device potentially dangerous.

While known bar stabilization systems do not have the foregoing disadvantages, these known bar systems rely solely on adhesion through cheek pads which have no mechanical clasping. Therefore, the bar is permitted to torque, allowing for excessive movement of the bar and excessive movement of the attached tube. Additionally, the tube can rotate around the bar, allowing it to kink in the patient's larynx, restricting air flow, or placing extended tube pressure on the palate, causing interference with normal palatal development.

In an attempt to relieve palatal pressure, plates have been designed to rest on the tube to prevent tube extended contact with the palate. However, these plates interfere with oral hygiene and are difficult and clumsy to place properly.

What is needed is a stabilization method that allows for securing tracheal and/or gastric tubes and other medical devices without applying tape to the face, maintains visibility of tube markings, and keeps the infant's face visible to parents and caregivers. It should also prevent kinking of the tube and allow for attachment of additional anchorage when heavier loads (such as nasal continuous positive airway pressure (NCPAP) prongs) are applied, and prevent oral secretions from collecting and interfering with adhesion and/or causing infection.

By conceiving a method to stabilize medical devices that enter or cover the nose and/or mouth using mechanical advantage along with adhesives, the present invention fulfills this need, and further provides related advantages.

SUMMARY OF THE INVENTION

The present invention provides an apparatus and a method for stabilizing at least one medical device such as a tracheal or gastric tube entering or covering at least one facial cavity such as the mouth and/or nose. The present invention takes advantage of a transverse stent containing a docking platform to secure patient tracheal and/or gastric tubes without the need to apply tape to the face, while maintaining visibility of tube markings, preventing kinking of the tube, and keeping the infant's face visible to parents and caregivers. The transverse stent is secured to the patient's face using adhesive fixation and optional mechanical clamping. The novel present invention also allows for attachment of additional anchorage when heavier loads need to be stabilized.

In one form, the invention comprises a transverse stent comprising a superior border opposed to an inferior border, an inner surface and an outer surface. A first facial interface is attached to a first terminal end of the transverse stent, and positioned to adhesively adhere and mechanically clasp to a first side of a patient's face.

A second facial interface is attached to a second terminal end of the transverse stent and positioned to adhesively adhere and mechanically clasp to a second side of a patient's face. A docking platform attached to the outer surface of the transverse stent supports the medical device.

In a different form, the invention adds gutters positioned on the inner surface of the respective first and second terminal end proximate to the respective first and second facial interface to channel oral fluids away from the respective first and second facial interface.

One advantage of the present invention is that it provides an interface for the attachment of an assortment of medical devices that improves upon the limitations of current attachment methods. In particular, it avoids the use of adhesive tape applied to the face, while providing a more stable and a secure attachment of these devices.

Another advantage of the present invention is that it provides a stable tracheal tube holder and tracheal tube stent, thereby maintaining the angle the tube enters the mouth, and preventing movement or kinking of the tracheal tube. In this manner, the tracheal tube will not impinge upon the infants lip or palate, and therefore, will not negatively impact upon oral-facial growth and development.

Still another advantage of the present invention is that because the endotracheal tube is better stabilized, the risk of accidental extubation is significantly reduced. This increase in stabilization also prevents tube movement during mechanical ventilation, thereby lessening the potential for patient discomfort, desaturation spells and laryngal trauma.

Yet another advantage of the present invention is that the transverse stent is stronger and more resistant to bending and buckling than known stabilization systems. By providing the ability to easily add additional anchorage, heavier medical devices, such as nasal CPAP cannula, can be fully supported, thereby reducing patient discomfort associated with those heavier devices.

Other features and advantages of the present invention will be apparent from the following more detailed description of the preferred embodiment, taken in conjunction with the accompanying figures which illustrate, by way of example, the principles of the invention.

DETAILED DESCRIPTION OF THE PREFERRED EMBODIMENTS

The present invention sets forth a method and an apparatus for stabilizing at least one medical device entering at least one facial cavity. Such medical devices may include, for example, endotracheal tubes, nasotracheal tubes, nasalgastric tubes, naso or orojejunal tubes, nasal thermistors, nasal pneumotachometers, nasal capnographs, nasal masks, oxygen delivery tubing and nasal CPAP delivery systems, although the present invention will stabilize any device entering or covering the mouth or nose. For the purposes of this disclosure, the term "tube" is meant to include all such medical devices entering the mouth or nose, and that the present invention is not limited to stabilizing medical devices tubular in shape. Likewise, it should be understood that oral insertion, nasal insertion or both simultaneously will be stabilized equally well.

Figure 1:
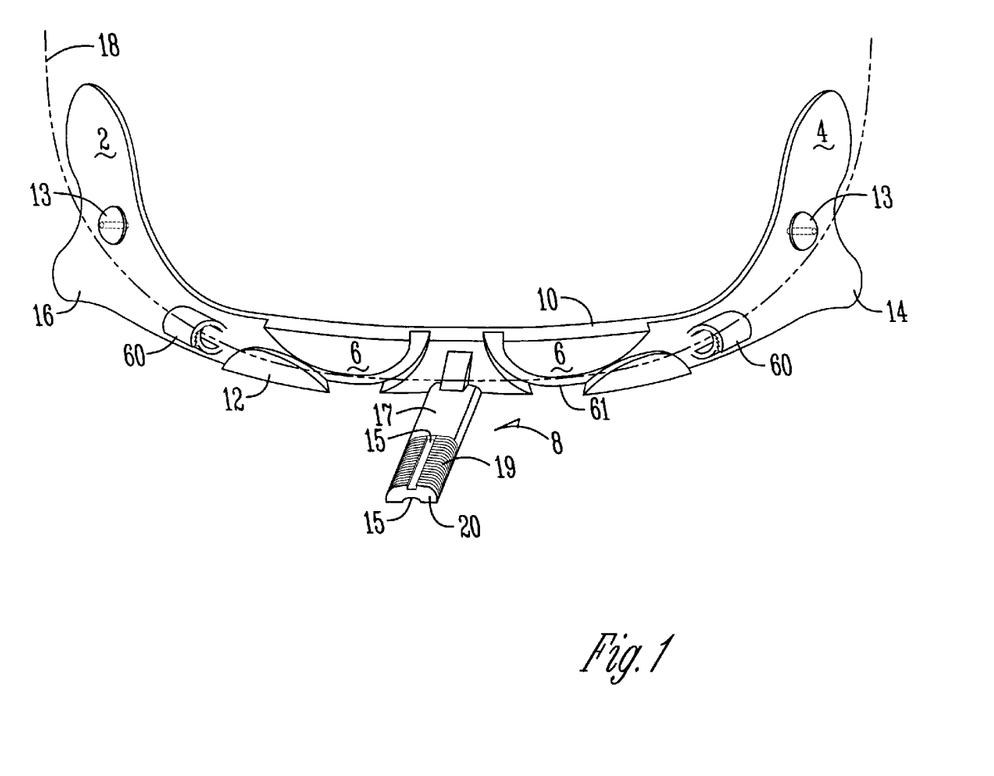
FIG. 1 is a frontal view of the present invention.
Figure 2:
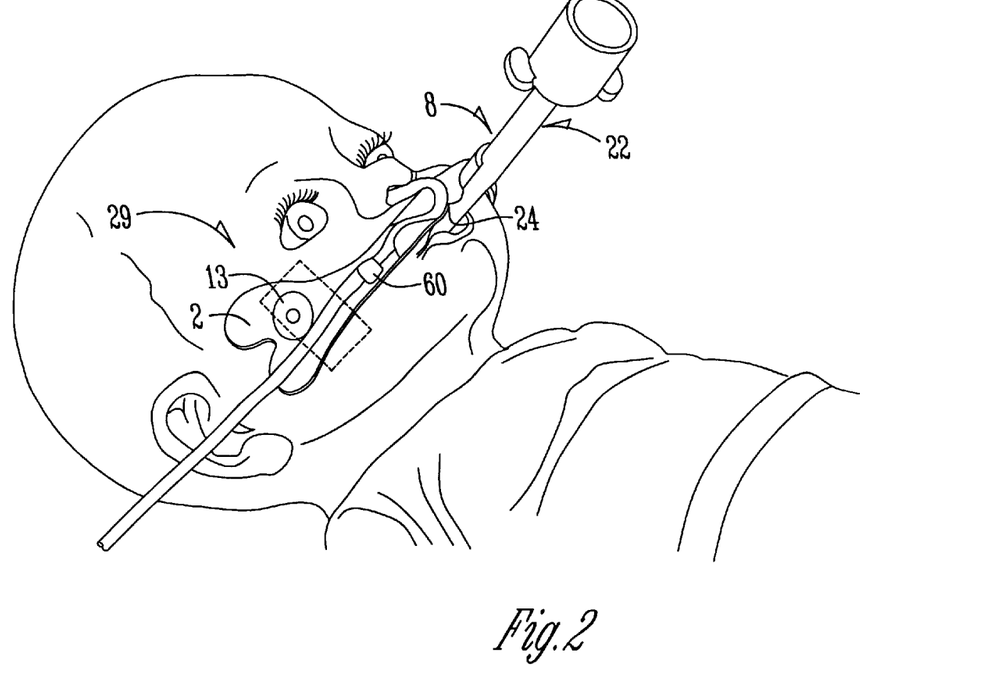
FIG. 2 is a representation of the invention stabilizing an endotracheal tube on an infant.

As shown in FIG. 1, the present invention comprises a first 2 and second 4 facial interface positioned on opposite terminal ends of a transverse stent 6 to mechanically and adhesively clasp both sides of a patient's face 29 (FIG. 2). A docking platform 8 is attached to the transverse stent 6 to support at least one medical device 22 (FIG. 2).

The transverse stent 6 is generally arch shaped so as to follow the contours of the patient's face 29, and of a length sufficient to permit the first 2 and second 4 facial interface to rest on the right and left sides of a patient's face 29, for example, on the right and left cheek. While the transverse stent 6 may take any shape in cross-section, for example, triangular, round or oval, in its preferred form, the transverse stent 6 is square or rectangular in cross-section, having a superior border 10 opposed to an inferior border 12, an inner surface 30 (FIG. 3) towards the patient's face 29 and an outer surface 14. These defined borders and surfaces allow for more precise placement of the docking platform 8 and optional mechanical clasps (discussed below). In a preferred embodiment, the transverse stent 6 is about 6 mm in width and about 2.5 mm deep. It will be understood, however, that both the width and depth will depend on the material used and the relative size of the patient.

When the first 2 and second 4 facial interfaces are in proper position on the patient's face 29, the transverse stent 6 should remain about 1 mm to about 3 mm above the maxillary, or upper, lip 24 (FIG. 2), so as to not interfere with or traumatize the lip 24 or trap debris between the transverse stent 6 and maxillary lip 24, and allow access for proper hygiene. The transverse stent 6 should be sufficiently rigid enough to support the attached medical device or devices 22, yet have the ability to yield slightly in a manner that will allow the first 2 and second 4 facial interfaces to approximate (move medially) if the patient were to lay with the head on one or the other side. The ability of the transverse stent to yield slightly in all directions helps to dissipate any displacement force applied to the medical device 22 or to the transverse stent 6, rather than directing the entire displacing force to the first 2 and second 4 facial interface.

While metals such as, for example, stainless steel, titanium, Ni—Cr and other alloys may be used, ideally the transverse stent 6 should be hypoallergenic and, optionally, clear so as to not obstruct visualization of the patient's face 29 or of the medical device 22 or any markings contained within or on the medical device 22. Materials useful for this purpose would include, for example, polymers such as, for example, polystyrene, polyurethane, polycarbonate, fiberglass and the like that preferably are transparent or translucent when polymerized.

The transverse stent 6 and/or facial interface 2, 4 may be manufactured into a variety of shapes and sizes that allow the clinician to choose the ideal transverse stent 6 and/or facial interface 2, 4 for the individual patient. Alternatively, at least a portion of the apparatus may be fabricated from a material that is pliable until activated, whereupon, once activated, the material sets to a clinician-predetermined shape. In this manner, the transverse stent 6 and/or facial interface 2, 4 in its pliable form may be custom molded to the patient's face 29 and then activated to take a permanent set.

This activation may take the form of, for example, a light-activated polymer in which a predetermined wavelength of a light is applied to the material to effect polymerization and, hence, the permanent set, or it may take the form of mixing two materials together to initiate an auto-polymerization, or the polymerization may be heat activated. Another alternative to establishing proper length of the transverse stent 6 is to cut the transverse stent 6 to its proper length prior to attachment, using known adhesive methods, of the first 2 and second 4 facial interface. Still another alternative (not shown) to establishing a clinician-predetermined length is for a first half of the transverse stent to be slidably contained, for example, using a tongue and groove, within, in front, or behind a second half of the transverse stent. Once the halves are slidably moved to establish the predetermined length, the halves are fixed in the predetermined length, for example, by crimping a metal band around the overlapping halves, or by stapling the halves within the overlapping portion.

The first 2 and second 4 facial interface are mirror images of one another and in the interest of brevity will not be described separately. It is to be understood that the second facial interface 4 mirrors the first facial interface 2 description which follows.

The facial interface 2 may be integrally fabricated as part of the transverse stent 6, or it may be separately fabricated and subsequently adhered, using known adhesives techniques, to the transverse stent 6. It may take any shape that provides a surface area of sufficient size to effectuate adequate adhesion to the patient's face 29 once adhesive is applied. The facial interface 2 may be substantially flat or it may be substantially contoured to follow the contours of a patient's face 29. It must be stiff enough to resist deformation when a displacement force is applied to the transverse stent 6.

Ideally, the surface area should be minimized so as to cover the least amount of the patient's face possible yet maintain adequate resistance to displacement forces. In a preferred embodiment, the facial interface 2 is generally "Y" in shape. While the advantages of the transverse stent 6 are obtained when the facial interface 2 is adhesively adhered to the patient's face 29 by a substantially flat facial interface 2, ideally, the facial interface 2 should: mechanically clasp, as well as adhesively adhere to the patient's face 29. For the purposes of this disclosure, the term "mechanically clasp" is meant to include resistance to movement through primarily physical forces, for example, frictional forces; and the term "adhesively adhere" is meant to include the bonding of two substances together by interfacial forces, for example, valence forces, interlocking action, or both. In a preferred embodiment, the facial interface 2 is fabricated from the same material as the transverse stent 6, such material having plastic properties that allow contouring of the facial interface 2 to the patient's face 29. It is the contour which provides the mechanical clasping. Ideally, the facial interface 2 is positioned such that at least a portion of the inferior border 16 of the facial interface 2 is contoured to overlie at least a portion of an inferior border of a patient's mandible 23. For the purposes of this invention, the term "overlie an inferior border of a patient's mandible" means resting on a facial skin surface which covers the inferior border of the mandible.

For example, to achieve this mechanical clasping, the inferior border 16 of the facial interface 2 is rotated medially about 5 degrees to about 35 degrees around the line 18; longitudinally bisecting the transverse stent 6. This rotation of the facial interface 2 inferior border 16 may be pre-molded into the apparatus, or alternatively, if the facial interface 2 is fabricated separately and subsequently adhered to the transverse stent 6, the appropriate rotation is maintained while adhering the facial interface 2 to the transverse stent 6. The mechanical clasping, acting synergistically with an adhesive applied to the facial interface 2, provides increased resistance to transverse stent 6 displacement forces.

The adhesive may be pre-applied to the facial interface 2 and covered with a protective, removable backing (not shown), for example, polyurethane, cellophane or other backing material, as is well known in the art, which is removed prior to placement, or the adhesive may be applied directly to the patient's face 29 prior to seating the facial interface 2. When the facial interface 2 is seated, the adhesive layer should extend beyond the edge of the interface 2 to spread and reduce the adhesive forces on the skin. The adhesive is, for example, any protective adhesive that is nonirritating and, optionally, transparent to fragile newborn facial tissue, of sufficient viscosity to allow for controlled placement and spreading, allows for easy removal of excess adhesive, and permits for easy removal of the facial interface 2 (preferably with water) when desired, without damaging the underlying tissue. Examples of such adhesives: are water-based adhesives such as hydrogel adhesives sold through Ludlow, and pectin based adhesives, for example, Duoderm Extrathin, manufactured by Convatec, Inc. and Comfeel, manufactured by Coloplast Company.

The medical device 22, for example, an endotracheal tube, is fixed, for example, taped, to a docking platform 8. In a preferred embodiment, the docking platform 8 is a cantilevered finger 20, molded as part of the transverse stent 6, projecting from the inferior border 12 of the transverse stent 6 at a predetermined angle, for example, about 65 degrees to about 115 degrees, preferably about 95 degrees, although it should be understood that any predetermined angle allowing for fixation of the medical device 22 is acceptable. Optionally, the most distal portion 19 of the cantilevered finger 20, about 35 mm in length is substantially flexible while the medial portion 17, about 15 mm in length is substantially rigid. In this manner, some or all of a medical device displacement force will be dissipated through the flexible portion 19 before reaching the transverse stent 6. At least one optional channel 15 may be molded into at least one surface, preferably the top surface, of the cantilevered finger 20 for receiving a medical device 22, for example, a tube. Affixing a tube to the cantilevered finger 20 prevents the tube from kinking.

Optionally, the cantilevered finger 20 may extend from the superior border 10 of the transverse stent 6 for support of nasal tubes (not shown). The cantilevered finger 20 may be molded on the top, bottom or both surfaces for receiving and fixing a medical device 22, for example, an endotracheal tube or CPAP prongs.

It should be understood that the docking platform 8 may extend from the transverse stent at any angle required to make the docking platform 8 functional. This may range from a negative angle, as might be required, for example, for medical devices entering the nose, to an angle of about 180 degrees.

The docking platform 8 may be located anywhere along the length of the transverse stent 6 to meet specific clinical indications. Likewise, the docking platform 8 may project from the outer surface 14 at the superior border 10, the inferior border 12, or anywhere within the body of the transverse stent 6, or may span the transverse stent 6 from the superior border 10 to the inferior border 12, as clinically indicated.

Figure 4A:
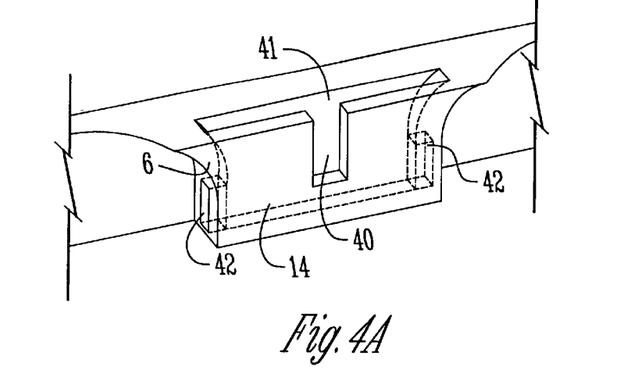
FIGS. 4a–4c are a representation of a universal docking station.
Figure 4B:
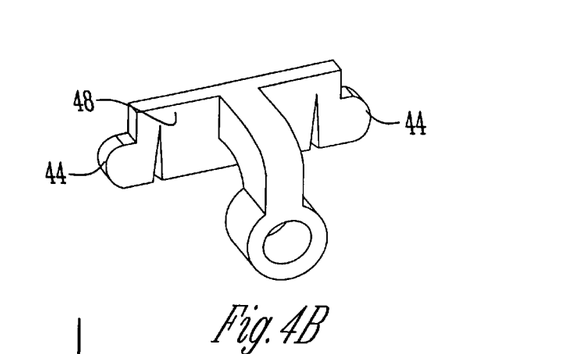
Figure 4C:
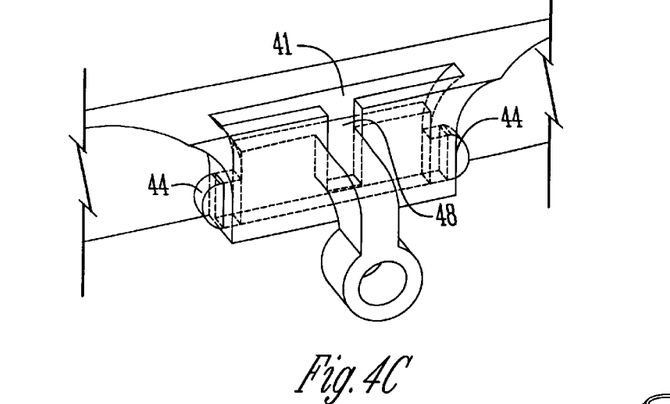
Figure 4D:
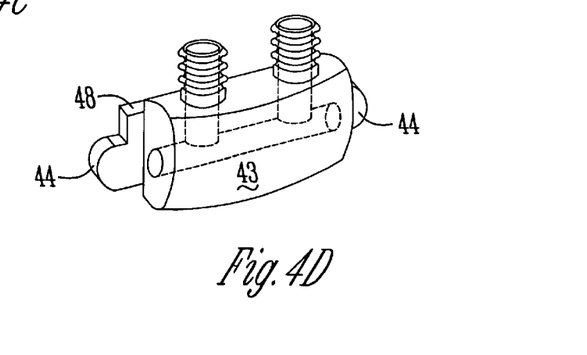
FIG. 4d is a representation of a nasal CPAP cannula.

In another embodiment of the device, shown in FIGS. 4(a)–(d), a universal docking station 41 is fabricated into outer surface 14 at, for example, as shown in FIG. 4(a), the center of the transverse stent 6. The universal docking station 41 is, for example, a recess 40 to removably receive a projection, or other form of docking design that would permit the removable attachment of medical devices such as, for example, a CPAP cannula 48, using, for example, a snap fit arrangement (described below).

Alternatively, the docking platform 8 may be removably mounted to the universal docking station 41 using, for example, the snap fit arrangement or tongue and groove. The groove 40 molded within the universal docking station has slots 42 to mechanically engage docking platform tabs 44 extending from the docking platform tongue 48. The tabs 44 are urged, such as by spring-loading, so that they may be disengaged for easy removal of the docking platform 8. The transverse stent 6 may include more than one universal docking station 41 to provide flexibility positioning the docking platform 8 on the transverse stent 6.

Figure 7:
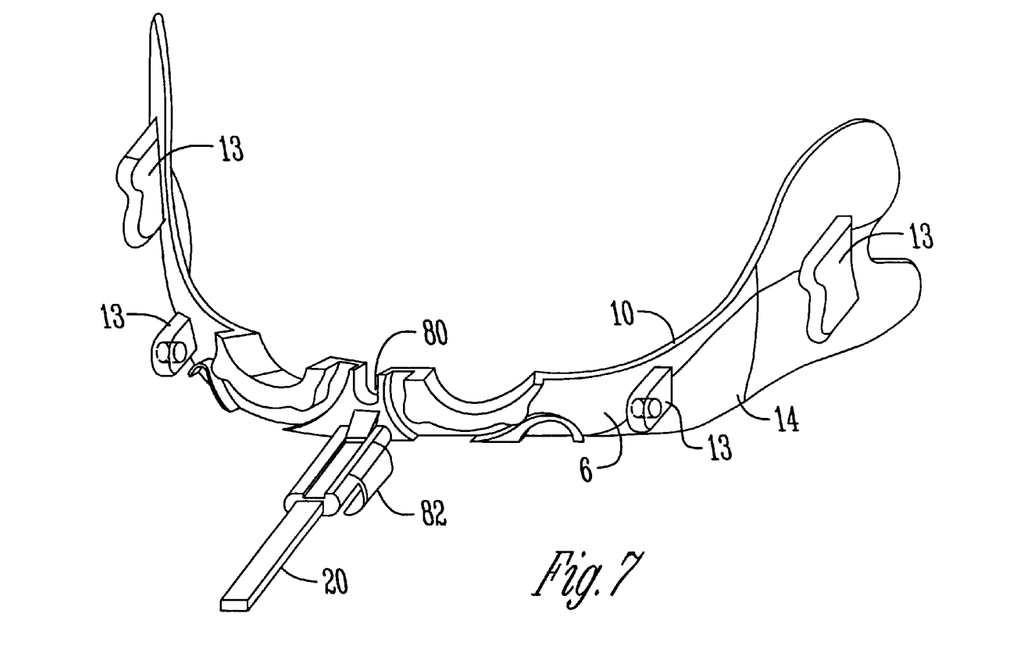
FIG. 7 is an oblique view of a representation of a different embodiment depicting the clamp.

A heavier medical device 22 attached to the docking platform 8 may require additional stabilization anchorage. As shown in FIGS. 1 and 7, optional anchorage attachment 13 is positioned on the outer surface 14 of the apparatus for receiving an attachment point of at least one additional anchorage such as, for example, a head strap, chin strap or both (not shown). The anchorage attachment 13 may be any attachment that allows for easy attachment and removal of the additional anchorage, such as, for example, a button, hook, hook and loop, slot, tab, combinations thereof and the like.

Figure 3:
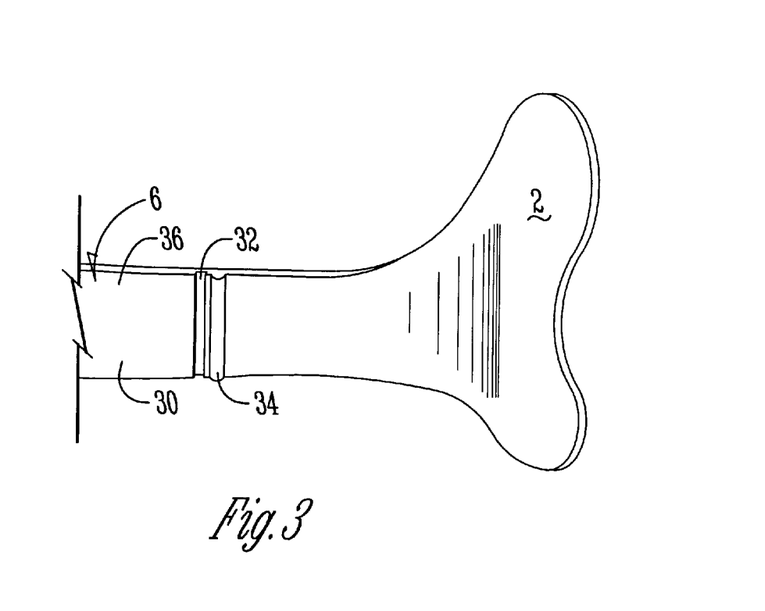
FIG. 3 is a view of the inner surface of the transverse stent.

In still another embodiment, shown in FIG. 3, to prevent oral secretions from interacting with and interfering with the adhesive bond, and/or collecting and harboring bacteria, gutters 32 are fabricated into the inner surface 30 of the terminal ends 36 of the transverse stent 6, proximate to the facial interface 2, 4, to channel oral fluids away from the facial interface 2,4. These gutters 32 may take the form of, for example, a channel or groove molded into the inner surface 30 of the transverse stent 6 traversing the stent 6 from the superior border 10 to the inferior border 12. An optional raised lip 34 running parallel and distal to the gutter 32 provides further protection from oral fluid contamination of the adhesive.

Figure 5:
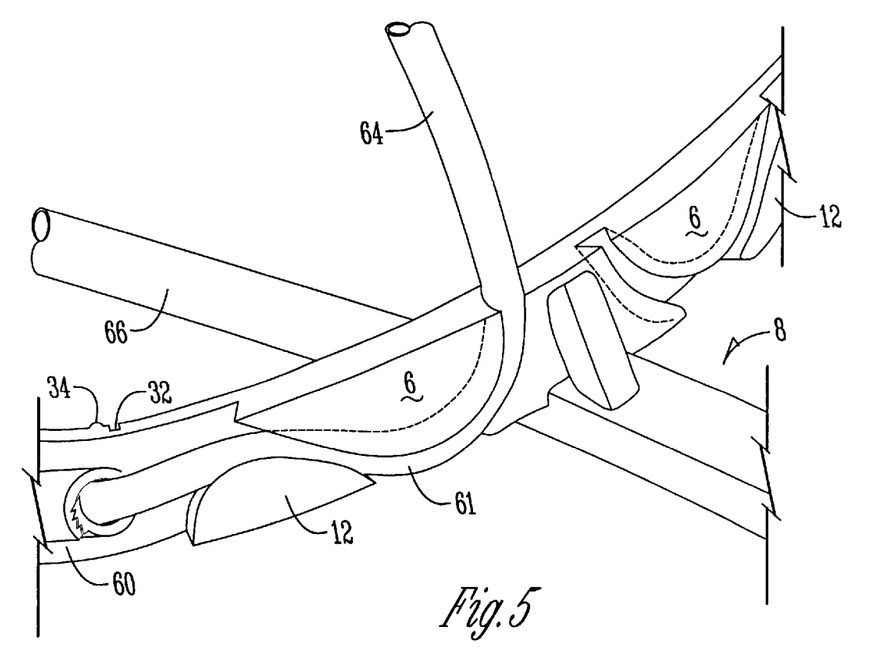
FIG. 5 is a representation of an endotracheal tube and a nasalgastric tube supported concurrently.

Returning to FIG. 1, optionally, the transverse stent 6 has one or more mechanical retaining points, such as clasps 60 or channel 61, to removably receive a portion of at least one medical device 22, for example a portion of a tube. The mechanical retaining points may be mechanically, chemically or metallurgically attached to the outer surface 14 of the transverse stent 6 using known methods, such as welding, bolting or screwing, or they may be integrally molded as part of the transverse stent outer surface 14. The at least one clip 60 and/or channel 61 are appropriately sized to mechanically retain a tube to the transverse stent 6, as shown in FIG. 5. The mechanical retaining points, such as the clasps 60 and channel 61 are particularly useful in, for example, retaining a nasalgastric tube 64 used in combination with an endotracheal tube 66.

Figure 6:
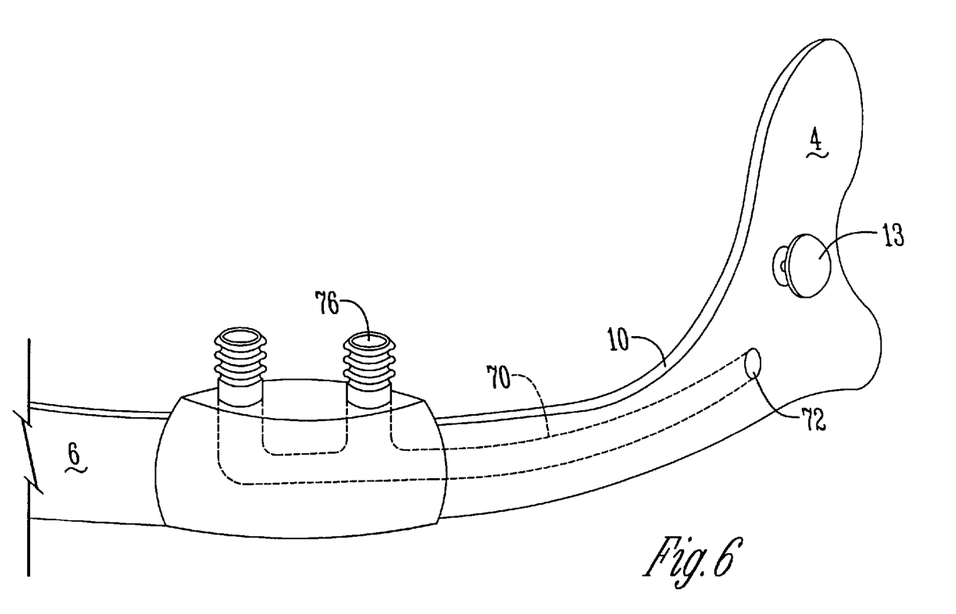
FIG. 6 is a representation of a different embodiment depicting the hollow bore.

In yet another embodiment, shown in FIG. 6, a hollow bore 70 of predetermined diameter is fabricated within the transverse stent 6 to transport a supply of gas, for example, a medical gas (not shown). The bore 70 has a first opening 72 at the distal end of the apparatus to receive the medical gas, and a second opening 76 at the docking station 8 to deliver the medical gas. The bore 70 runs substantially longitudinally through the interior of the transverse stent 6.

Figure 8:
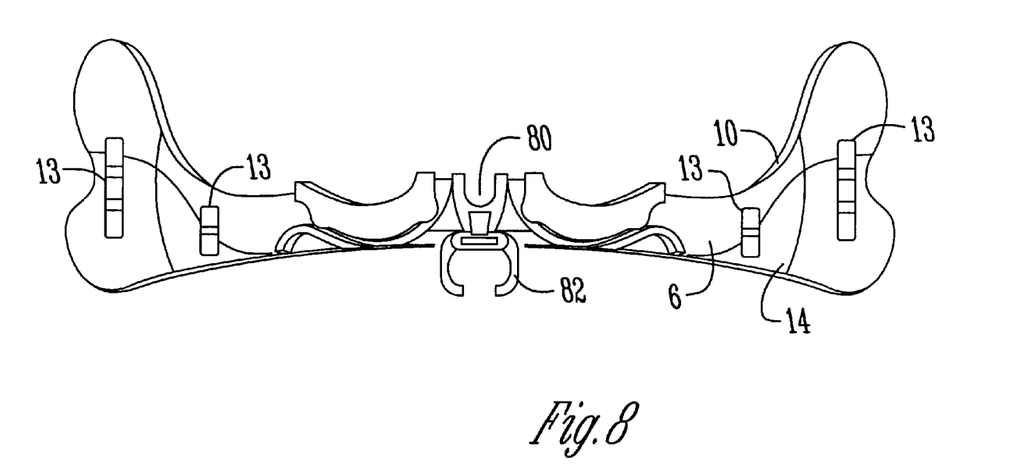
FIG. 8 is a frontal view of the embodiment of FIG. 7.

In still another embodiment, shown in FIGS. 7 and 8, a groove 80 fabricated, for example, in the center of the superior border 10 of the transverse stent 6 further supports tubes that enter the nose, for example, feeding tubes, CPAP prongs and oxygen tubes. A clamp 82 may optionally be molded to the bottom surface of the cantilevered finger 20. The clamp 82 is fabricated to be urged, such as by spring loading to surround a medical device 22, for example, an endotracheal tube. The clamp 82 only partially surrounds the tube, allowing a portion of the exposed tube to adhere to adhesive tape (not shown).

The clamp 82 can accommodate tubes of varying sizes. In a preferred embodiment, the clamp 82 can accommodate tubes with internal diameters of about 2.5 mm to about 3.5 mm. The clamp must be of sufficient length to supportively engage the tube, preferably about half the length of the substantially rigid portion of the cantilevered finger 20. In a preferred embodiment, this length is about 6.5 mm to about 8.5 mm, most preferably about 7.5 mm. Optionally, the tube is further supported to the cantilevered finger 20 with adhesive tape covering, for example, the full length of the cantilevered finger 20, including the clamp 82. When desirable to remove the clamp, such as when the patient is nasally intubated, the clamp is removed by, for example, cutting, twisting or grinding. Optionally, the clamp may be fabricated to removably attach to the cantilevered finger 20, for example, as in the manner described above with the universal docking station 41.

In use, the present invention would operate as follows: After clinically determining the appropriate size and shape of the transverse stent 6 and the amount of mechanical clasping needed, a properly fitted stabilizing apparatus is either selected from stock or custom fabricated bedside.

After the medical device 22 has been delivered to the patient, for example, after the endotracheal tube has been inserted, adhesive is applied to the predetermined area of the face 29, or, alternatively, if the facial interface 2, 4 is preloaded with adhesive, the protective backing, for example, an adhesive release liner, is removed. The facial interface 2, 4 is placed on the face 29 and adhered to position the transverse stent 6 above the patient's maxillary lip 24 in the predetermined position.

Once the adhesive has set, the medical device 22 is removably fixed to the docking platform 8, for example, by taping or clamping. In the preferred embodiment, the endotracheal tube 66 is taped to the cantilevered finger 20. If, for example, a nasalgastric tube 64 is also in use, that is removably affixed to the docking platform 8, or alternatively, removably fixed by the optional mechanical clasps 60 on the outer surface 14 of the transverse stent 6. If additional anchorage is required, head or chin straps are removably affixed to the anchorage attachments 13.

With the present invention in place, the oral cavity presents easy access for support staff to main proper hygiene. Markings on the tubes, for example, indicators to insure proper tube insertion are clearly visible. Once stabilized, tubes maintain their original position, avoiding the risk of accidental extubation, laryngal trauma, or adverse influence on oral-facial growth and development.

Should emergency removal of the tubes be required, the tape affixing the tube to the docking platform may be quickly and easily cut, or alternatively, the transverse stent may be easily and quickly cut from the facial interface, allowing the tube and transverse stent to be removed simultaneously.

The present invention also comprises the system for stabilizing at least one medical device entering at least one facial cavity formed by the above described method.

Although the present invention has been described in connection with specific examples and embodiments, those skilled in the art will recognize that the present invention is capable of other variations and modifications within its scope. These examples and embodiments are intended as typical of, rather than in any way limiting on, the scope of the present invention as presented in the appended claims.

What I claim is:

1. An apparatus for stabilizing at least one medical device entering at least one facial cavity of a patient's face comprising:
    a transverse stent having a superior border, the superior border having a first end and a second end, an inferior border opposed to the superior border, the inferior border having a first end and a second end, an outer surface extending between the superior border and the inferior border from the first end of the superior border and the inferior border to the second end of the superior border and the inferior border, an inner surface extending between the superior border and the inferior border from the first end of the superior border and the inferior border to the second end of the superior border and the inferior border, the outer surface facing away from a facial cavity and opposed to the inner surface;
    first facial interface attached to a first end of the transverse stent, the first end extending between the first end of the superior border of the transverse stent and the first end of the inferior border of the transverse stent, wherein the first facial interface includes a surface positioned adjacent a first side of the patient's face;
    a second facial interface attached to a second end of the transverse stent, the second end extending between the second end of the superior border of the transverse stent and the second end of the inferior border of the transverse stent, wherein the second facial interface includes a surface positioned adjacent a second side of the patient's face;
    a docking platform attached to the outer surface of the transverse stent at a preselected angle, the docking platform for supporting at least one medical device;
    and means for attaching the first and second facial interfaces to the first and second sides of the patient's face, the means for attaching comprising structure to mechanically clasp a patient's face.

2. The apparatus of claim 1 wherein the means for attaching the first and second facial interfaces to the first and second sides of the patient's face is selected from the group consisting of adhesively adhering, mechanically clasping and combinations thereof.

3. The apparatus of claim 2 wherein the means for attaching includes a hydrocolloid adhesive.

4. The apparatus of claim 2 wherein the means for attaching includes a pectin based adhesive.

5. The apparatus of claim 2 wherein the means for attaching includes a substantially transparent, hypoallergenic adhesive.

6. The apparatus of claim 1 wherein the transverse stent is of a predetermined length sufficient to provide mechanical clasping to the first and second sides of the patient's face.

7. The apparatus of claim 1 wherein each of the first and second facial interfaces further includes an inferior border, at least a portion of each of the inferior borders of the first and second facial interface mechanically clasping an area of the patient's face overlying at least a portion of an inferior border of a patient's mandible.

8. The apparatus of claim 7 wherein the at least a portion of the inferior border of the first and second facial interface are each offset medially about 5 degrees to about 35 degrees from a plane substantially parallel to the respective first and second side of the patient's face to mechanically clasp an area of the patient's face overlying at least a portion of the inferior border of a mandible of the patient.

9. The apparatus of claim 1 wherein the means for attaching the first and second facial interfaces to the first and second sides of the patient's face is an adhesive intermediate the facial interface and the patient's face.

10. The apparatus of claim 9 wherein the first and second facial interfaces are substantially contoured to a contour of the respective first and second side of the patient's face.

11. The apparatus of claim 1 wherein the means for attaching the first and second facial interfaces to the first and second sides of the patient's face is an adhesive applied to the first and second sides of the patient's face intermediate the facial interface and the face.

12. The apparatus of claim 11 wherein the first and second facial interfaces are substantially contoured to a contour of the respective first and second side of the patient's face.

13. The apparatus of claim 1 wherein the transverse stent is substantially arch shaped to position the transverse stent a predetermined distance above a maxillary lip of the patient.

14. The apparatus of claim 13 wherein the transverse stent is positioned about 1 mm to about 3 mm above the patient's maxillary lip.

15. The apparatus of claim 1 wherein the transverse stent is comprised of a material that is substantially transparent and hypo-allergenic.

16. The apparatus of claim 1 wherein at least a portion of the apparatus is fabricated from a pliable, activatable material capable of being activated to achieve a permanent predetermined shape after the apparatus is contoured to the predetermined shape.

17. The apparatus of claim 1 further including at least one anchorage attachment to receive an attachment point from at least one additional anchorage.

18. The apparatus of claim 1 wherein the at least one anchorage attachment is positioned on a surface opposed to the surfaces adjacent to the patient's face.

19. The apparatus of claim 17 wherein the at least one anchorage attachment is selected from the group consisting of button, hook, loop, slot, tab and combinations thereof.

20. The apparatus of claim 1 wherein the transverse stent further comprises a first and second gutter positioned on the inner surface of the transverse stent proximate to the respective first and second facial interfaces, positioned to channel oral fluids away from the respective first and second facial interface after attachment to the patient's face.

21. The apparatus of claim 1 wherein the transverse stent further comprises at least one mechanical retaining point to removably receive the at least one medical device, the at least one mechanical retaining point selected from the group consisting of a clip positioned on the stent outer surface, a channel positioned in the stent outer surface and combinations thereof.

22. The apparatus of claim 1 wherein the transverse stent further comprises a hollow bore of predetermined diameter positioned to transport a gas, the bore comprising a first opening in the transverse stent to receive the supply of the gas and a second opening at the docking station to deliver the supply of the gas.

23. The apparatus of claim 1 wherein the docking platform is permanently attached to the outer surface.

24. The apparatus of claim 1 wherein the docking platform is removably attached to the outer surface.

25. The apparatus of claim 1 wherein a universal docking station is fabricated within a surface of the transverse stent to removably receive the docking platform.

26. The apparatus of claim 25 wherein the universal docking station is a recess that removably receives a projection extending from the docking platform.

27. The apparatus of claim 1 wherein the docking platform comprises a cantilevered finger extending from the transverse stent.

28. The apparatus of claim 27 wherein the cantilevered finger extends outward at an angle of about 95 degrees.

29. The apparatus of claim 27 wherein the cantilevered finger includes a substantially flexible section of predetermined length and a substantially rigid section of predetermined length, the rigid section extending from the stent and the flexible length extending from the rigid length.

30. The apparatus of claim 27 wherein the cantilevered finger further includes at least one channel positioned on at least one surface of the cantilevered finger for receiving the at least one medical device.

31. The apparatus of claim 30 wherein the at least one channel includes a first channel positioned on a top surface of the cantilevered finger and a second channel positioned on a bottom surface of the cantilevered finger.

32. The apparatus of claim 27 wherein the cantilevered finger further includes a clamp attached to a bottom surface of the cantilevered finger, the clamp removably engaging the at least one medical device.

33. The apparatus of claim 1 wherein the docking platform is a CPAP cannula.

34. The apparatus of claim 1 wherein the transverse stent further includes a groove in the superior surface to support the at least one medical device.

35. The apparatus of claim 1 wherein each facial interface is curved between inferior and superior borders.

36. The apparatus of claim 1 wherein each facial interface includes an anterior portion and a posterior portion, and the facial interface is curved between anterior and posterior portions.

37. The apparatus of claim 1 wherein the transverse stent has a middle and further comprising an open area at or near the middle of the transverse stent along said superior border.

38. The apparatus of claim 1 wherein each facial interface has perimeter dimensions larger than the stent between facial interfaces, the facial interfaces shaped to substantially conform to contours of the patient's face, but having substantial stiffness.

39. An apparatus for stabilizing at least one medical device entering at least one facial cavity comprising:
   a transverse stent positioned between a first and second facial interface, the first facial interface opposed to the second facial interface;
   the first facial interface positioned adjacent a first side of a patient's face;
   the second facial interface positioned adjacent a second side of a patient's face;
   a means for supporting at least one medical device with the transverse stent;
   a means for adhesively adhering the first and second facial interfaces to the first and second sides of the patient's face; and
   a means for mechanically clasping the first and second facial interfaces to the first and second sides of the patient's face.

40. The apparatus of claim 39 wherein each facial interface is curved between inferior and superior borders.

41. The apparatus of claim 39 wherein each facial interface includes an anterior portion and a posterior portion, and the facial interface is curved between anterior and posterior portions.

42. The apparatus of claim 39 wherein the transverse stent has a middle and further comprising an open area at or near the middle of the transverse stent along said superior border.

43. The apparatus of claim 39 wherein each facial interface has perimeter dimensions larger than the stent between the facial interfaces, the facial interfaces shaped to substantially conform to contours of the patient's face, but having substantial stiffness.

44. A method for stabilizing at least one medical device entering at least one facial cavity of a patient's face comprising the steps of:
   selecting at least one medical device;
   inserting a first end of the at least one medical device into at least one facial cavity;
   attaching a stabilizer to the patient's face, the stabilizer comprising:
      a transverse stent having a superior border with a first end and a second end, an inferior border opposed to the superior border, the inferior border having a first end and a second end, an outer surface extending between the superior border and the inferior border from the first end of the superior border and the inferior border to the second end of the superior border and the inferior border, an inner surface extending between the superior border and the inferior border from the first end of the superior border and the inferior border to the second end of the superior border and the inferior border, the outer surface facing away from a facial cavity and opposed to the inner surface;
      a first facial interface attached to a first end of the transverse stent, the first end extending between the first end of the superior border and the first end of the inferior border, wherein the first facial interface is positioned adjacent a first side of the patient's face;
      a second facial interface attached to a second end of the transverse stent, the second end extending between the second end of the superior border and the second end of the inferior border, wherein the second facial interface is positioned adjacent a second side of the patient's face;
      a docking platform attached to the outer surface of the transverse stent at a preselected angle, the docking platform for supporting the at least one medical device; and
      a means for attaching the first and second facial interfaces to the first and second sides of the patient's face, the means for attaching comprising structure to mechanically clasp a patient's face; and
   affixing a second end of the at least one medical device to the stabilizer.

45. The method of claim 44 wherein the at least one medical device is selected from the group consisting of endotracheal tubes, nasaltracheal tubes, nasogastric tubes, orogastric tubes, nasojejunal tubes, orojejunal tubes, nasal thermistors, nasal pneumotachometers, nasal capnographs oxygen tubing, oxygen cannula, nasal CPAP delivery systems, nasal mask and face mask.

46. A system for stabilizing at least one medical device entering at least one facial cavity formed by the method of claim 44.

47. An apparatus for stabilizing at least one medical device entering at least one facial cavity of a patient's face comprising:

a transverse stent having a superior border, the superior border having a first end and a second end, an inferior border opposed to the superior border, the inferior border having a first end and a second end, an outer surface extending between the superior border and the inferior border from the first end of the superior border and the inferior border to the second end of the superior border and the inferior border, an inner surface extending between the superior border and the inferior border from the first end of the superior border and the inferior border to the second end of the superior border and the inferior border, the outer surface facing away from a facial cavity and opposed to the inner surface, the inner surface being substantially flat and having a distance between the superior and inferior border of the inner surface approximately at least one-third a distance between upper lip and nose of a patient at a portion of the stent adapted for placement at and near a patient's nose to allow the transverse stent some medial flex but deter flexing in other directions;

first facial interface attached to a first end of the transverse stent, the first end extending between the first end of the superior border of the transverse stent and the first end of the inferior border of the transverse stent, wherein the first facial interface includes a surface positioned adjacent a first side of the patient's face;

a second facial interface attached to a second end of the transverse stent, the second end extending between the second end of the superior border of the transverse stent and the second end of the inferior border of the transverse stent, wherein the second facial interface includes a surface positioned adjacent a second side of the patient's face;

a docking platform attached to the outer surface of the transverse stent at a preselected angle, the docking platform for supporting at least one medical device.

48. The apparatus of claim 47 comprising a means for attaching the first and second facial interfaces to the first and second sides of the patent's face is selected from the group consisting of adhesively adhering, mechanically clasping and combinations thereof.

49. The apparatus of claim 48 wherein the means for attaching includes a substantially transparent, hypoallergenic adhesive.

50. The apparatus of claim 47 wherein the transverse stent is of a predetermined length sufficient to provide mechanical clasping to the first and second sides of the patient's face.

51. The apparatus of claim 47 wherein each of the first and second facial interfaces further includes an inferior border, at least a portion of each of the inferior borders of the first and second facial interface mechanically clasping an area of the patient's face overlying at least a portion of an inferior border of a patient's mandible.

52. The apparatus of claim 47 wherein at least a portion of the inferior border of the first and second facial interface are each offset medially about 5 degrees to about 35 degrees from a plane substantially parallel to the respective first and second side of the patient's face to mechanically clasp an area of the patient's face overlying at least a portion of the inferior border of a mandible of the patient.

53. The apparatus of claim 47 wherein the first and second facial interfaces are substantially contoured to a contour of the respective first and second side of the patient's face.

54. The apparatus of claim 47 wherein the transverse stent is substantially arch shaped to position the transverse stent a predetermined distance above a maxillary lip of the patient.

55. The apparatus of claim 47 wherein the transverse stent is comprised of a material that is substantially transparent and hypo-allergenic.

56. A method for stabilizing at least one medical device entering at least one facial cavity of a patient's face comprising the steps of:

selecting at least one medical device;

inserting a first end of the at least one medical device into at least one facial cavity;

attaching a stabilizer to the patient's face, the stabilizer comprising:

a transverse stent having a superior border with a first end and a second end, an inferior border opposed to the superior border, the inferior border having a first end and a second end, an outer surface extending between the superior border and the inferior border from the first end of the superior border and the inferior border to the second end of the superior border and the inferior border, an inner surface extending between the superior border and the inferior border from the first end of the superior border and the inferior border to the second end of the superior border and the inferior border, the inner surface being substantially flat and having a distance between the superior and inferior border of the inner surface approximately at least one-third a distance between upper lip and nose of a patient at a portion of the stent adapted for placement at and near a patient's nose to allow the transverse stent some medial flex but deter flexing in other directions, the outer surface facing away from a facial cavity and opposed to the inner surface;

a first facial interface attached to a first end of the transverse stent, the first end extending between the first end of the superior border and the first end of the inferior border, wherein the first facial interface is positioned adjacent a first side of the patient's face;

a second facial interface attached to a second end of the transverse stent, the second end extending between the second end of the superior border and the second end of the inferior border, wherein the second facial interface is positioned adjacent a second side of the patient's face;

a docking platform attached to the outer surface of the transverse stent at a preselected angle, the docking platform for supporting the at least one medical device; and a component adapted to attach the first and second facial interfaces to the first and second sides of the patient's face; and affixing a second end of the at least one medical device to the stabilizer.

57. The method of claim 56 wherein the stabilizer is adapted to attach the first and second facial interfaces to the first and second sides of the patent's face by one or more of adhesively adhering, mechanically clasping and combinations thereof.

58. The method of claim 56 wherein the step of attaching includes a substantially transparent, hypoallergenic adhesive.

59. The method of claim 56 wherein the transverse stent is of a predetermined length sufficient to provide mechanical clasping to the first and second sides of the patient's face.

60. The method of claim 56 wherein each of the first and second facial interfaces further includes an inferior border, at least a portion of each of the inferior borders of the first and second facial interface mechanically clasping an area of the patient's face overlying at least a portion of an inferior border of a patient's mandible.

61. The method of claim 56 wherein the at least a portion of the inferior border of the first and second facial interface are each offset medially about 5 degrees to about 35 degrees from a plane substantially parallel to the respective first and second side of the patient's face to mechanically clasp an area of the patient's face overlying at least a portion of the inferior border of a mandible of the patient.

62. The method of claim 56 wherein the first and second facial interfaces are substantially contoured to a contour of the respective first and second side of the patient's face.

63. The method of claim 56 wherein the transverse stent is substantially arch shaped to position the transverse stent a predetermined distance above a maxillary lip of the patient.

64. The method of claim 56 wherein the transverse stent is comprised of a material that is substantially transparent and hypo-allergenic.

* * * * *